United States Patent [19]
Liston et al.

[11] Patent Number: 4,632,771
[45] Date of Patent: Dec. 30, 1986

[54] NORMALLY LIQUID $C_{14}$ TO $C_{18}$ MONOALKYL CATECHOLS

[75] Inventors: Thomas V. Liston, San Rafael; Warren Lowe, El Cerrito; Vernon R. Small, Rodeo, all of Calif.

[73] Assignee: Chevron Research Company, San Francisco, Calif.

[21] Appl. No.: 711,797

[22] Filed: Mar. 14, 1985

Related U.S. Application Data

[63] Continuation-in-part of Ser. No. 641,910, Aug. 17, 1984, abandoned.

[51] Int. Cl.[4] .............. C10M 129/00; C10M 137/10
[52] U.S. Cl. .................................. 252/32.7 E; 252/33; 252/39; 252/40; 252/52 R; 568/766
[58] Field of Search ................. 252/52 R, 32.7 E; 568/766

[56] References Cited

U.S. PATENT DOCUMENTS

| | | | |
|---|---|---|---|
| 2,429,905 | 10/1947 | Wright | 252/52 R |
| 2,795,548 | 6/1957 | Thomas et al. | 252/49.6 |
| 3,554,945 | 1/1971 | Andress et al. | 252/57 R |
| 3,649,538 | 3/1972 | Hotten | 252/49.3 |

OTHER PUBLICATIONS

Smalheer et al., "Lubricant Additives", 1967, Ch. 1.

*Primary Examiner*—William R. Dixon, Jr.
*Assistant Examiner*—Cynthia A. Prezlock
*Attorney, Agent, or Firm*—S. R. LaPaglia; R. C. Gaffney; G. F. Swiss

[57] ABSTRACT

This invention relates to normally liquid lubricating oil additives which provide both anti-oxidant and friction-modifying properties when added to lubricating oil. In particular, this invention relates to $C_{14}$ to $C_{18}$ alkyl catechol lubricating oil additives which are normally liquid at typical storage temperatures.

8 Claims, No Drawings

NORMALLY LIQUID $C_{14}$ TO $C_{18}$ MONOALKYL CATECHOLS

CROSS REFERENCE TO RELATED APPLICATIONS

This application is a continuation-in-part of pending application U.S. Ser. No. 641,910 filed Aug. 17, 1984, which is now abandoned.

BACKGROUND OF THE INVENTION

1. Field of the Invention

This invention relates to normally liquid lubricating oil additives which are multifunctional additives providing anti-oxidant, diesel deposit inhibition, and friction modifying properties when added to lubricating oil. In particular, this invention relates to $C_{14}$ to $C_{18}$ alkyl catechol lubricating oil additives which are normally liquid at typical storage temperatures. The alkyl catechols of this invention are useful multifunctional lubricating oil additives providing anti-oxidant, diesel deposit inhibition, and boundary friction-reducing properties for the lubricating oil.

2. Prior Art

Certain alkyl catechols are known in the art as anti-oxidant additives for lubricating oils. In particular, Wright, U.S. Pat. No. 2,429,905, discloses para-substituted stearylcatechol and other para-substituted lower alkyl catechols as possessing anti-oxidant properties. Similarly, Andress et al., U.S. Pat. No. 3,554,945, discloses polyhydroxy benzenoid compounds as useful antioxidant additives for lubricating oils. Although alkylated products prepared from a $C_{15}$–$C_{20}$ mixed olefin fraction are disclosed, Andress et al. do not specifically disclose $C_{15}$–$C_{20}$ monoalkylated catechols or that alkyl catechol compositions would possess friction modifying properties.

Thomas et al., U.S. Pat. No. 2,795,548, is another prior art reference which discloses alkyl catechols. In particular, Thomas et al. disclose alkyl catechols containing 2 to 18 carbon atoms in the alkyl group which are employed as intermediates in the preparation of borated alkyl catechols.

In addition to their anti-oxidant and diesel deposit inhibition properties, it has now been found that longer chain monoalklyl catechol of 14 carbon atoms or more possess improved boundary friction-reducing properties than do shorter chain monoalkyl catechols (those of less than 14 carbon atoms). Accordingly, when employing alkyl catechol additives in a lubricating oil, it is desirable to employ longer chain alkyl catechols.

However, there is a problem with the use of longer chain alkyl catechols since the preparation of these catechols often results to some degree in the occurrence of solidification or haziness in the product. The degree of this problem ranges from alkyl catechols which are a solid wax at room temperature to liquid alkyl catechols containing wax particles at room temperature. In any case, the solidification or haziness requires that prior to formulation the solid particles or haziness must be removed by either heating the alkyl catechol which adds an additional step to the overall process or by adding sufficient diluent oil to the alkyl catechol which increases the cost of transporting this additive.

Although shorter chain alkyl catechols would alleviate this solidification problem, the use of these shorter chain alkyl catechol would be at the expense of improved boundary friction. Accordingly, there is a need to develop an alkyl catechol which is normally liquid at typical storage temperatures while maintaining sufficient alkyl chain length to impart multifunctional properties such as anti-oxidant, diesel deposit inhibition, and boundary friction-reducing properties to the lubricant oil.

It has now been found that $C_{14}$ to $C_{18}$ monoalkyl catechols prepared from a mixture of at least three $C_{14}$, $C_{15}$, $C_{16}$, $C_{17}$, and $C_{18}$ linear alpha-olefins and containing less than 20% $C_{18}$ alkyl content are normally liquid at typical storage temperatures. Moreover, the $C_{14}$ to $C_{18}$ alkyl chain length imparts multifunctional properties to the lubricating oil. The liquid characteristic of the $C_{14}$ to $C_{18}$ monoalkyl catechols of this invention is particularly surprising in view of the fact that a monoalkyl catechol prepared from a mixture of $C_{18}$, $C_{19}$, $C_{20}$ and $C_{21}$ linear alpha-olefins, as well as those prepared from a mixture of $C_{14}$, $C_{16}$ and $C_{18}$ linear alpha olefins with greater than 20% $C_{18}$ content contain some solidification.

SUMMARY OF THE INVENTION

This invention relates to normally liquid $C_{14}$ to $C_{18}$ monoalkyl catechols which are useful lubricating oil additives. In particular, this invention is directed to a normally liquid alkyl catechol which comprises a monoalkyl catechol wherein the alkyl substituent is a mixture of at least three of $C_{14}$, $C_{15}$, $C_{16}$, $C_{17}$, and $C_{18}$ alkyl groups derived from the corresponding $C_{14}$, $C_{15}$, $C_{16}$, $C_{17}$ and $C_{18}$ linear alpha-olefin with the proviso that the $C_{18}$ alkyl content is less than 20% of the total alkyl content. Monoalkyl catechols may be represented by the formula

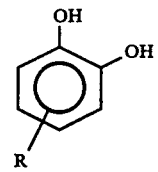

wherein R is a mixture of at least three of $C_{14}$, $C_{15}$, $C_{16}$, $C_{17}$, and $C_{18}$ alkyl groups derived from linear alphaolefins. In all cases, the $C_{18}$ alkyl content must be maintained below 20% of all of alkyl groups in order to maintain a liquid product.

Preferably, $C_{18}$ alkyl content is maintained below 15%.

A particularly preferred group of $C_{14}$ to $C_{18}$ alkylcatechols are the alkyl catechols derived from $C_{14}$ to $C_{18}$ cracked wax alpha-olefins.

$C_{14}$ to $C_{18}$ cracked wax alpha-olefins are readily prepared as described in U.S. Pat. No. 3,883,417 which is incorporated herein for its teaching of the preparation of cracked wax olefins.

Another preferred linear alpha-olefin for use in the preparation of the alkyl catechols of this invention are those derived from an ethylene growth process. The ethylene growth process may be accomplished by a high temperature ethylene oligomerization employing a nickel chelate catalyst. Another method is that described in U.S. Pat. No. 2,889,385 which is incorporated herein by reference for its teaching of the "ethylene growth" preparation of olefins. Mixtures of $C_{14}$, $C_{16}$, and $C_{18}$ linear alpha-olefins are commercially available from Shell Chemicals, Houston, Tex., and sold under the name Neodene ®.

In addition to possessing anti-oxidant and diesel deposit inhibition properties, the $C_{14}$ to $C_{18}$ monoalkyl catechols of this invention possess boundary friction-modifying properties. Thus, another aspect of this invention relates to a lubricating oil composition comprising an oil of lubricating viscosity and an effective amount to reduce friction of a $C_{14}$ to $C_{18}$ monoalkyl catechol of Formula I above.

Other additives may also be present in the lubricating oil in order to obtain a proper balance of properties such as dispersion, anticorrosion, antiwear, and antioxidation which are critical for the proper operation of an internal combustion engine.

Thus, still another aspect of the present invention is directed to a lubricating oil composition especially useful in the crankcase of an internal combustion engine for the purpose of improving the fuel consumption of said engine comprising:

(a) a major amount of an oil of lubricating viscosity; and (b) an effective amount of each of the following:
1. an alkenyl succinimide,
2. a Group II metal salt of a dihydrocarbyl dithiophosphoric acid,
3. a neutral or overbased alkali or alkaline earth metal hydrocarbyl sulfonate or mixtures thereof,
4. a neutral or overbased alkali or alkaline earth metal alkylated phenate or mixtures thereof, and
5. a $C_{14}$ to $C_{18}$ monoalkyl catechol friction modifier.

Further, in accordance with the invention, there is provided a method for reducing fuel consumption of an internal combustion engine by treating the moving surfaces thereof with the lubricating oil composition described above.

As used herein, the term "monoalkyl catechol" means a product obtained by reacting essentially stoichiometric amounts of a mixture of $C_{14}$ to $C_{18}$ alpha-olefins to the pyrocatechol. Such products generally contain some amounts of dialkyl catechol. Stoichiometric amounts of the $C_{14}$ to $C_{18}$ alpha-olefin to the pyrocatechol are generally from 0.9:1 to 1.2 to 1, although preferably 1:1 to 1.1:1.

As used herein, the term "at least three of $C_{14}$, $C_{15}$, $C_{16}$, $C_{17}$ and $C_{18}$ alkyl derived from a linear alpha olefin" means that the mixture of a $C_{14}-C_{18}$ linear alpha olefin used to alkylate the catechol must contain minimally three components of at least 1% (one percent) each; preferably at least 5% each and most preferably at least 10% each.

The term "linear alpha-olefin" means that the alpha-olefins are predominately linear with less than 10%, preferably 5%, of the alpha-olefins in the mixture contain branching

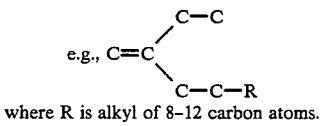

where R is alkyl of 8-12 carbon atoms.

Also as used herein, the term "normally liquid" means that the $C_{14}$ to $C_{18}$ monoalkyl catechols will be liquid at typical storage temperatures and atmospheric pressure without any wax or haziness present. The term "typical storage temperatures" means from 15° C. to 25° C.

DETAILED DESCRIPTION OF THE INVENTION

The normally liquid $C_{14}$ to $C_{18}$ monoalkyl catechols of Formula I are prepared by alkylating pyrocatechol with a mixture of at least three of $C_{14}$ to $C_{18}$ linear alpha-olefins containing less than 20% $C_{18}$ content.

For instance, the alkyl catechols of the Formula I may be prepared by reacting a straight-chained (linear) alpha-olefin containing 14 to 18 carbon atoms with pyrocatechol in the presence of an alkylating catalyst at a temperature of from about 60° C. to 200° C., and preferably 125° C. to 180° C. in an essentially inert solvent at atmospheric pressure. A preferred alkylating catalyst is a sulfonic acid catalyst such as Amberlyst 15 ® available from Rohm and Haas, Philadelphia, Pa. Molar ratios of reactants may be used and preferably a 10% by weight molar excess of linear alpha-olefin over catechol is used. Examples of the inert solvents include benzene, toluene, chlorobenzene, and 250 Thinner which is a mixture of aromatics, paraffins, and naphthenes.

The alkyl catechols of this invention are generally of the formula

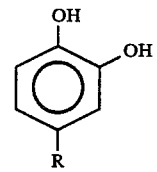

wherein R is a mixture of at least three of $C_{14}$, $C_{15}$, $C_{16}$, $C_{17}$, and $C_{18}$ alkyl groups. Also, up to 25% by weight and preferably 15% by weight of the alkyl catechols may have the R group in a position adjacent or ortho to one of the hydroxy groups and has the Formula III

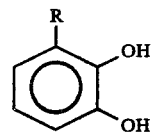

wherein R is defined above.

Although Applicants do not want to be limited by any theory, it is believed that the alkyl catechol product containing a mixture of at least three $C_{14}$ to $C_{18}$ linear alpha-olefins and less than 20% $C_{18}$ content will break up the crystallinity and results in a liquid product. However, as the $C_{18}$ alkyl content rises above about 20%, the ability of the resulting mixed alkyl groups to inhibit crystallinity in the alkyl catechol is impaired. Accordingly, it is necessary that the alpha-olefin mixture employed in preparing the alkyl catechols of this invention be prepared from a mixture of at least three of $C_{14}$ to $C_{18}$ linear alpha-olefins wherein the $C_{18}$ content is maintained below 20% and preferably below 15%.

The liquid characteristic of the mixture of $C_{14}-C_{18}$ alkyl-catechol containing less than 20% alkyl content is particularly surprising in view of the fact that if a single species of linear alpha olefin (e.g., $C_{16}$) is employed to alkylate the catechol, the resulting alkyl catechol nevertheless contains mixtures. These mixtures result from the isomerization of the olefinic bond by the acidic alkylation catalyst as depicted in reactions (I) and (II) below wherein a $C_{16}$ alpha-olefin is employed for illustrative purposes:

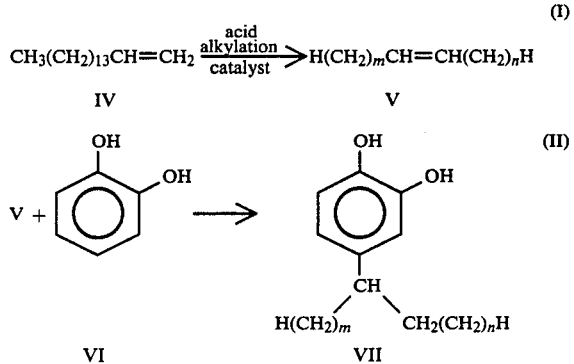

wherein m and n are independently integers from 0 to 14 with the sum of m+n equals 14. It is readily apparent that alkylation of pyrocatechol, VI, by a single linear alpha-olefin species results in a mixture of products containing different m and n values. Yet as noted in Table I, $C_{16}$ and $C_{18}$ alkyl catechols prepared from the corresponding linear alpha-olefin contain solidification.

In view of the isomerization of the olefinic bond in the alpha-olefin by the acidic alkylation catalyst, the term "alpha-olefin" as used herein also includes olefins isomerized from the corresponding alpha-olefin.

Also included within the scope of this invention are fully formulated lubricating oils containing from about 0.5 to 5% by weight of a $C_{14}$ to $C_{18}$ alkyl catechols of this invention. Contained in the fully formulated composition is:

1. an alkenyl succinimide,
2. a Group II metal salt of a dihydrocarbyl dithiophosphoric acid,
3. a neutral or overbased alkali or alkaline earth metal hydrocarbyl sulfonate or mixtures thereof, and
4. a neutral or overbased alkali or alkaline earth metal alkylated phenate or mixtures thereof.

The alkenyl succinimide is present to act as a dispersant and prevent formation of deposits formed during operation of the engine. The alkenyl succinimides are well-known in the art. The alkenyl succinimides are the reaction product of a polyolefin polymer-substituted succinic anhydride with an amine, preferably a polyalkylene polyamine. The polyolefin polymer-substituted succinic anhydrides are obtained by reaction of a polyolefin polymer or a derivative thereof with maleic anhydride. The succinic anhydride thus obtained is reacted with the amine compound. The preparation of the alkenyl succinimides has been described many times in the art. See, for example, U.S. Pat. Nos. 3,390,082; 3,219,666; and 3,172,892, the disclosure of which are incorporated herein by reference. Reduction of the alkenyl substituted succinic anhydride yields the corresponding alkyl derivative. The alkyl succinimides are intended to be included within the scope of the term "alkenyl succinimide". A product comprising predominantly mono- or bis-succinimide can be prepared by controlling the molar ratios of the reactants. Thus, for example, if one mole of amine is reacted with one mole of the alkenyl or alkyl substituted succinic anhydride, a predominantly mono-succinimide product will be prepared. If two moles of the succinic anhydride are reacted per mole of polyamine, a bis-succinimide will be prepared.

Particularly good results are obtained with the lubricating oil compositions of this invention when the alkenyl succinimide is a polyisobutene-substituted succinic anhydride of a polyalkylene polyamine.

The polyisobutene from which the polyisobutene-substituted succinic anhydride is obtained by polymerizing isobutene and can vary widely in its compositions. The average number of carbon atoms can range from 30 or less to 250 or more, with a resulting number average molecular weight of about 400 or less to 3,000 or more. Preferably, the average number of carbon atoms per polyisobutene molecule will range from about 50 to about 100 with the polyisobutenes having a number average molecular weight of about 600 to about 1,500. More preferably, the average number of carbon atoms per polyisobutene molecule ranges from about 60 to about 90, and the number average molecular weight ranges from about 800 to 1,300. The polyisobutene is reacted with maleic anhydride according to well-known procedures to yield the polyisobutene-substituted succinic anhydride.

In preparing the alkenyl succinimide, the substituted succinic anhydride is reacted with a polyalkylene polyamine to yield the corresponding succinimide. Each alkylene radical of the polyalkylene polyamine usually has up to about 8 carbon atoms. The number of alkylene radicals can range up to about 8. The alkylene radical is exemplified by ethylene, propylene, butylene, trimethylene, tetramethylene, pentamethylene, hexamethylene, octamethylene, etc. The number of amino groups generally, but not necessarily, is one greater than the number of alkylene radicals present in the amine, i.e., if a polyalkylene polyamine contains 3 alkylene radicals, it will usually contain 4 amino radicals. The number of amino radicals can range up to about 9. Preferably, the alkylene radical contains from about 2 to about 4 carbon atoms and all amine groups are primary or secondary. In this case, the number of amine groups exceeds the number of alkylene groups by 1. Preferably the polyalkylene polyamine contains from 3 to 5 amine groups. Specific examples of the polyalkylene polyamines include ethylenediamine, diethylenetriamine, triethylenetetramine, propylenediamine, tripropylenetetramine, tetraethylenepentamine, trimethylenediamine, pentaethylenehexamine, di-(trimethylene)triamine, tri(hexamethylene)tetramine, etc.

Other amines suitable for preparing the alkenyl succinimide useful in this invention include the cyclic amines such as piperazine, morpholine and dipiperazines.

Preferably the alkenyl succinimides used in the compositions of this invention have the following formula

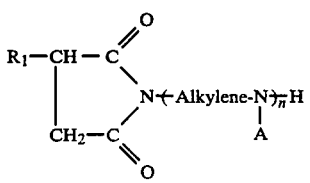

wherein:
(a) $R_1$ represents an alkenyl group, preferably a substantially saturated hydrocarbon prepared by polymerizing aliphatic monoolefins. Preferably $R_1$ is prepared from isobutene and has an average number of carbon atoms and a number average molecular weight as described above;

(b) the "Alkylene" radical represents a substantially hydrocarbyl group containing up to about 8 carbon atoms and preferably containing from about 2–4 carbon atoms as described hereinabove;

(c) A represents a hydrocarbyl group, an amine-substituted hydrocarbyl group, or hydrogen. The hydrocarbyl group and the amine-substituted hydrocarbyl groups are generally the alkyl and amino-substituted alkyl analogs of the alkylene radicals described above. Preferably A represents hydrogen;

(d) n represents an integer of from about 1 to 10, and preferably from about 3–5.

The alkenyl succinimide is present in the lubricating oil compositions of the invention in an amount effective to act as a dispersant and prevent the deposit of contaminants formed in the oil during operation of the engine. The amount of alkenyl succinimide can range from about 1 percent to about 20 percent weight of the total lubricating oil composition. Preferably the amount of alkenyl succinimide present in the lubricating oil composition of the invention ranges from about 1 to about 10 percent by weight of the total composition.

The alkali or alkaline earth metal hydrocarbyl sulfonates may be either petroleum sulfonate, synthetically alkylated aromatic sulfonates, or aliphatic sulfonates such as those derived from polyisobutylene. One of the more important functions of the sulfonates is to act as a detergent and dispersant. These sulfonates are well-known in the art. The hydrocarbyl group must have a sufficient number of carbon atoms to render the sulfonate molecule oil soluble. Preferably, the hydrocarbyl portion has at least 20 carbon atoms and may be aromatic or aliphatic, but is usually alkylaromatic. Most preferred for use are calcium, magnesium or barium sulfonates which are aromatic in character.

Certain sulfonates are typically prepared by sulfonating a petroleum fraction having aromatic groups, usually mono- or dialkylbenzene groups, and then forming the metal salt of the sulfonic acid material. Other feedstocks used for preparing these sulfonates include synthetically alkylated benzenes and aliphatic hydrocarbons prepared by polymerizing a mono- or diolefin, for example, a polyisobutenyl group prepared by polymerizing isobutene. The metallic salts are formed directly or by metathesis using well-known procedures.

The sulfonates may be neutral or overbased having base numbers up to about 400 or more. Carbon dioxide and calcium hydroxide or oxide are the most commonly used material to produce the basic or overbased sulfonates. Mixtures of neutral and overbased sulfonates may be used. The sulfonates are ordinarily used so as to provide from 0.3% to 10% by weight of the total composition. Preferably, the neutral sulfonates are present from 0.4% to 5% by weight of the total composition and the overbased sulfonates are present from 0.3% to 3% by weight of the total composition.

The phenates for use in this invention are those conventional products which are the alkali or alkaline earth metal salts of alkylated phenols. One of the functions of the phenates is to act as a detergent and dispersant. Among other things, it prevents the deposition of contaminants formed during high temperature operation of the engine. The phenols may be mono- or polyalkylated.

The alkyl portion of the alkyl phenate is present to lend oil solubility to the phenate. The alkyl portion can be obtained from naturally occurring or synthetic sources. Naturally occurring sources include petroleum hydrocarbons such as white oil and wax. Being derived from petroleum, the hydrocarbon moiety is a mixture of different hydrocarbyl groups, the specific composition of which depends upon the particular oil stock which was used as a starting material. Suitable synthetic sources include various commercially available alkenes and alkane derivatives which, when reacted with the phenol, yield an alkylphenol. Suitable radicals obtained include butyl, hexyl, octyl, decyl, dodecyl, hexadecyl, eicosyl, tricontyl, and the like. Other suitable synthetic sources of the alkyl radical include olefin polymers such as polypropylene, polybutylene, polyisobutylene and the like.

The alkyl group can be straight-chained or branch-chained, saturated or unsaturated (if unsaturated, preferably containing not more than 2 and generally not more than 1 site of olefinic unsaturation). The alkyl radicals will generally contain from 4 to 30 carbon atoms. Generally when the phenol is monoalkyl-substituted, the alkyl radical should contain at least 8 carbon atoms. The phenate may be sulfurized if desired. It may be either neutral or overbased and if overbased will have a base number of up to 200 to 300 or more. Mixtures of neutral and overbased phenates may be used.

The phenates are ordinarily present in the oil to provide from 0.2% to 27% by weight of the total composition. Preferably, the neutral phenates are present from 0.2% to 9% by weight of the total composition and the overbased phenates are present from 0.2 to 13% by weight of the total composition. Most preferably, the overbased phenates are present from 0.2% to 5% by weight of the total composition. Preferred metals are calcium, magnesium, strontium or barium.

The sulfurized alkaline earth metal alkyl phenates are preferred. These salts are obtained by a variety of processes such as treating the neutralization product of an alkaline earth metal base and an alkylphenol with sulfur. Conveniently the sulfur, in elemental form, is added to the neutralization product and reacted at elevated temperatures to produce the sulfurized alkaline earth metal alkyl phenate.

If more alkaline earth metal base were added during the neutralization reaction than was necessary to neutralize the phenol, a basic sulfurized alkaline earth metal alkyl phenate is obtained. See, for example, the process of Walker et al., U.S. Pat. No. 2,680,096. Additional basicity can be obtained by adding carbon dioxide to the basic sulfurized alkaline earth metal alkyl phenate. The excess alkaline earth metal base can be added subsequent to the sulfurization step but is conveniently added at the same time as the alkaline earth metal base is added to neutralize the phenol.

Carbon dioxide and calcium hydroxide or oxide are the most commonly used material to produce the basic or "overbased" phenates. A process wherein basic sulfurized alkaline earth metal alkylphenates are produced by adding carbon dioxide is shown in Hanneman, U.S. Pat. No. 3,178,368.

The Group II metal salts of dihydrocarbyl dithiophosphoric acids exhibit wear, antioxidant and thermal stability properties. Group II metal salts of phosphorodithioic acids have been described previously. See, for example, U.S. Pat. No. 3,390,080, columns 6 and 7, wherein these compounds and their preparation are described generally. Suitably, the Group II metal salts of the dihydrocarbyl dithiophosphoric acids useful in the lubricating oil composition of this invention contain from about 4 to about 12 carbon atoms in each of the hydrocarbyl radicals and may be the same or different and may be aromatic, alkyl or cycloalkyl. Preferred hydrocarbyl groups are alkyl groups containing from 4 to 8 carbon atoms and are represented by butyl, isobutyl, sec.-butyl, hexyl, isohexyl, octyl, 2-ethylhexyl and the like. The metals suitable for forming these salts include barium, calcium, strontium, zinc and cadmium, of which zinc is preferred.

Preferably, the Group II metal salt of a dihydrocarbyl dithiophosphoric acid has the following formula:

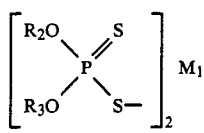

wherein:
(e) $R_2$ and $R_3$ each independently represent hydrocarbyl radicals as described above, and
(f) $M_1$ represents a Group II metal cation as described above.

The dithiophosphoric salt is present in the lubricating oil compositions of this invention in an amount effective to inhibit wear and oxidation of the lubricating oil. The amount ranges from about 0.1 to about 4 percent by weight of the total composition, preferably the salt is present in an amount ranging from about 0.2 to about 2.5 percent by weight of the total lubricating oil composition. The final lubricating oil composition will ordinarily contain 0.025 to 0.25% by weight phosphorus and preferably 0.05 to 0.15% by weight.

The finished lubricating oil may be single or multigrade. Multigrade lubricating oils are prepared by adding viscosity index (VI) improvers. Typical viscosity index improvers are polyalkyl methacrylates, ethylene propylene copolymers, styrene-diene copolymers and the like. So-called decorated VI improvers having both viscosity index and dispersant properties are also suitable for use in the formulations of this invention.

The lubricating oil used in the compositions of this invention may be mineral oil or in synthetic oils of viscosity suitable for use in the crankcase of an internal combustion engine. Crankcase lubricating oils ordinarily have a viscosity of about 1300 cst 0° F. to 22.7 cst at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha-olefins having the proper viscosity. Especially useful are the hydrogenated liquid oligomers of $C_6$ to $_{12}$ alpha-olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Additive concentrates are also included within the scope of this invention. In the concentrate additive form, the $C_{14}$-$C_{18}$ alkyl catechol of this invention is present in a concentration ranging from 5% to 50% by weight.

Other additives which may be present in the formulation include rust inhibitors, foam inhibitors, corrosion inhibitors, metal deactivators, pour point depressants, anti-oxidants, and a variety of other well-known additives.

The following examples are offered to specifically illustrate the invention. These examples and illustrations are not to be construed in any way as limiting the scope of the invention.

EXAMPLES

Example 1

To a 3-liter flask, equipped with stirrer, Dean Stark trap, condensor and nitrogen inlet and outlet and 759 gms. of a mixture of $C_{15}$ to $C_{18}$ alpha-olefin wherein the olefin mixture is characterized as containing 2% $C_{14}$; 30% $C_{15}$; 30% $C_{16}$; 28% $C_{17}$; and 10% $C_{18}$, 330 gms. of pyrocatechol, 165 gms. of a sulfonic acid cation exchange resin (polystyrene cross-linked with divinylbenzene) catalyst (Amberlyst 15 ® available from Rohm and Haas, Philadelphia, Pa.) and 240 ml. toluene. Heat the reaction mixture to 150° C. to 160° C. for about 7 hours with stirring under a nitrogen atmosphere. Strip the reaction mixture by heating to 160° C. under vacuum (0.4 mm Hg). Filter the product hot over super cell (SCC) to afford 930 g of a liquid $C_{15}$ to $C_{18}$ alkylsubstituted pyrocatechol. The product had a hydroxyl number of 259.

EXAMPLE 2

To a 3-liter flask, equipped with stirrer, Dean Stark trap, condensor and nitrogen inlet and outlet add 759 gms. of a mixture of $C_{14}$, $C_{16}$, and $C_{18}$ alpha-olefin, 330 gms. of pyrocatechol, 165 gms. of a sulfonic acid cation exchange resin (polystyrene cross-linked with divinylbenzene) catalyst (Amberlyst 15 ® available from Rohm and Haas, Phila., Pa.) and 220 ml. toluene. Heat the reaction mixture to 150° C. to 160° C. for about ½ hour with stirring under a nitrogen atmosphere. Add an additional 45 ml toluene. Continue heating the reaction mixture to 150° C. to 160° C. for 3 additional hours under nitrogen atmosphere. Filter the reaction mixture (~75° C.) over super cell (SCC). Strip the filtrate by heating to 160° C. under vacuum (0.4 mm Hg) to afford a liquid $C_{14}$, $C_{16}$, and $C_{18}$ alkyl-substituted pyrocatechol.

By following the processes of the above Examples, the following alkyl catechols were prepared and are listed in Table I below:

TABLE I

Compounds of the formula:

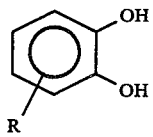

| Example | 1* | 2* | 3* | 4* | 5* | 6* | 7* | 8* | 9* | 10* |
|---|---|---|---|---|---|---|---|---|---|---|
| R Alkyl | 2% $C_{14}$ 30% $C_{15}$ 30% $C_{16}$ 28% $C_{17}$ 10% $C_{18}$ | 66% $C_{14}$ 33% $C_{16}$ 1% $C_{18}$ | 17% $C_{14}$ 46% $C_{16}$ 36% $C_{18}$ | 52% $C_{14}$ 26% $C_{16}$ 20% $C_{18}$ | 22% $C_{14}$ 58% $C_{16}$ 20% $C_{18}$ | 43% $C_{14}$ 22% $C_{16}$ 34% $C_{18}$ | 100% $C_{16}$ | 100% $C_{18}$ | 100% p-stearyl | 24% $C_{18}$ 37% $C_{19}$ 30% $C_{20}$ 9% $C_{21}$ |
| Physical Characteristics | Clear oil | Clear oil | Hazy semi-gelatinous with dispersed crystal solids | Hazy oil with dispersed crystal solids (borderline) | Hazy oil with dispersed crystal solids (borderline) | Very hazy oil with a lot of crystal solids | Semi-crystalline | Semi-crystalline | Solid | oil + wax |

*Prepared from the corresponding linear alpha-olefins.
The physical characteristics of the resulting alkyl catechol listed in Table I was determined by observation after conducting the following procedure:
1. Chill the alkyl catechol for 20 minutes to −8° C.
2. Seed the alkyl catechol with crystals from $C_{18}$ alkyl catechol and chill to −8° C. for 25 minutes
3. Let samples stand at 17-22° C. for 28 days - observe physical characteristics of alkyl catechol. The purpose of this accelerated shelf-life test is to rapidly determine the physical characteristic of an alkyl catechol which would result after prolonged storage.

EXAMPLE 11

The monoalkyl catechol of Example 1 was tested in a Caterpillar 1-G2 test in which a single-cylinder diesel engine having a 5⅛" bore by 6½" stroke is operated under the following conditions: timing, degrees BTDC, 8; brake mean effective pressure, psi 141; brake horsepower 42; Btu's per minute 5850; speed, 1800 RPM; air boost, 53" Hg absolute, air temperature in, 255° F.; water temperature out, 190° F.; and sulfur in fuel, 0.4% w. At the end of each 12 hours of operation, sufficient oil is drained from the crackcase to allow addition of 1 quart of new oil. In the test on the lubricating oil compositions of this invention, the 1-G2 test is run for 60 hours. At the end of the noted time period, the engine is dismantled and rated for cleanliness. The Institute of Petroleum Test Number 247/69 merit rating system for engine wear and cleanliness, accepted by ASTM, API, and SAE, is the rating system used to evaluate the engine. The overall cleanliness is noted as WTD, which is the summation of the above numbers. Lower values represent cleaner engines.

The base oil used in this test is CIT-CON 350N base oil containing 1.63% of a 50% concentrate in oil of an isobutenyl succinimide, 1% of a 50% concentrate in oil of an isobutenyl bis-succinimide, 9 mmoles/kg calcium sulfonate, 10 mmoles/kg overbased calcium sulfonate, 10 mmoles/kg sulfurized calcium phenate, 8.25 mmoles/kg zinc dialkyl dithiophosphate, and 0.05% sulfated polyglycol.

The results of this test are reported in Table II.

TABLE II

Caterpillar 1-G2 Test

| Formulation | Top Grove Fill % | WTD |
|---|---|---|
| Base Formulation | 75 | 168 |
| Base Formulation + 2% of a $C_{14}$ to $C_{18}$ monoalkyl catechol of Example 1(a) | 42 | 110 |

EXAMPLE 12

Formulated oils containing 1% by weight of the monoalkyl catechol of Example 1 were prepared and tested in a Sequence III D Test method (according to ASTM Special Technical Publication 315H).

The comparisons in each test were made in a formulated base and RPM 10W30 containing 3.5% of a polyisobutenyl succinimide of triethylenetetramine, 30 mmoles kg overbased magnesium hydrocarbyl sulfonate, 20 mmoles/kg overbased sulfurized alkyl phenol, 18 mmoles/kg zinc di(2-ethylhexyl) dithiophosphate, and 5.5% of a polymethacrylate based viscosity index improver.

Sequence III D Test

The purpose of the test is to determine the effect of the additives on the oxidation rate of the oil and the cam and lifter wear in the valve train of an internal combustion engine at relatively high temperatures (about 149° C. bulk oil temperature during testing).

In this test, an Oldsmobile 350 CID engine was run under the following conditions:
Runs at 3,000 RPM/max. run time for 64 hours and 100 lb load;
Air/fuel* ratio=16.5/1, using * GMR Reference fuel (leaded);
Timing=31° BTDC;
Oil temperature=300° F.;
Coolant temperature in=235° F. - out 245° F.;
30" of water of back pressure on exhaust;
Flow rate of Jacket coolant=60 gal/min.;
Flow rate of rocker cover coolant=3 gal/min.;
Humidity must be kept at 80 grains of $H_2O$;
Air temperature controlled equal inlet equal 80° F.;
Blowby Breather Heat exchanger at 100° F.

The effectiveness of the additive is measured after 64 hours in terms of camshaft and lifter wear and % viscosity increase. The results are given in the following Table III.

TABLE III

| Sequence IIID Test | |
|---|---|
| Formulation | Viscosity Increase % at 64 hr |
| base | too viscous to measure |
| base + 1% compound prepared according to Example 1(a) | 250 |

EXAMPLE 13

Tests were carried out which demonstrate the reduction in boundary friction obtained by adding the alkyl catechols of this invention to lubricating oil compositions.

The test was conducted by adding formulated oils containing friction modifiers to a friction measuring bench test. The reference oil, MPG-1, was a 10 W 30 oil formulated with 3.5% of a succinimide, 20 mmoles of an overbased phenate, 30 mmoles of a magnesium sulfonate, 18 mmoles of a zinc dithiophosphate, and 8% of a VI improver. To this formulation were added friction modifiers at a concentration of 25 mmoles per 100 g. Table IV lists the several formulations, each containing one friction modifier.

The friction bench test consists of a cast-iron "bullet" riding on a A247 cast-iron disk. This assembly is contained within a cup to which the test oil is added.

Break-up began with a 10 minute run at 100 rpm and low load. Friction data were recorded at 100°, 150° and 300° C., at a speed of 0.8 rpm, and a load of 1 Kg. All tests were run twice. Results are contained in Table IV.

TABLE IV

Boundary Friction Reduction Obtained By Employing a Fully Formulated Oil Containing 25 mmole per 100 g of Oil of a Compound of the Formula:

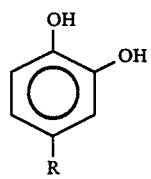

| R | 100° C. | σ | 150° C. | σ | 200° C. | σ |
|---|---|---|---|---|---|---|
| $C_6$ linear | 0.125 | 0 | 0.131 | 0.0014 | 0.139 | 0.0014 |

TABLE IV-continued

Boundary Friction Reduction Obtained By Employing a Fully Formulated Oil Containing 25 mmole per 100 g of Oil of a Compound of the Formula:

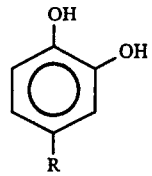

| R | 100° C. | σ | 150° C. | σ | 200° C. | σ |
|---|---|---|---|---|---|---|
| $C_{12}$ tetrapropenyl | 0.122 | 0.0021 | 0.122 | 0 | 0.126 | 0.0014 |
| $C_{12}$ linear | 0.108 | 0.0023 | 0.103 | 0.105 | 0.114 | 0.0220 |
| $C_{15-18}$ (mono) | 0.095 | 0 | 0.087 | 0.0086 | 0.089 | 0.0092 |
| $C_{18-30}$ | 0.085 | 0.0014 | 0.068 | 0.0035 | 0.068 | 0.0035 |
| MPG-1 (reference) | 0.120 | 0.0028 | 0.125 | 0 | 0.129 | 0.0049 |

σ — standard deviation

In Table IV above, below the temperature values are coefficients of friction for the oil at the temperature indicated-lower numbers indicate superior results.

What is claimed is:

1. A normally liquid alkyl catechol consisting essentially of a monoalkyl catechol wherein the alkyl substituent is a mixture of at least three of $C_{14}$, $C_{15}$, $C_{16}$, $C_{17}$, and $C_{18}$ alkyl groups wherein said alkyl is derived from a linear alpha-olefin and with the proviso that the $C_{18}$ alkyl content is less than 20% percent.

2. A normally liquid monoalkyl catechol as defined in claim 1 wherein the alkyl substituent is a mixture of $C_{14}$, $C_{16}$, and $C_{18}$ alkyl groups.

3. A normally liquid monoalkyl catechol as defined in claim 1 wherein the alkyl substituent is a mixture of $C_{14}$, $C_{15}$, $C_{16}$, $C_{17}$ and $C_{18}$ alkyl groups.

4. A lubricating oil composition comprising an oil of lubricating viscosity and from about 0.5 to 5% by weight of a compound defined in claim 1.

5. A lubricating oil composition as defined in claim 4 which additionally contains:
   (a) from about 1% to 20% by weight of an alkenyl succinimide or alkenyl succinate or mixtures thereof;
   (b) from about 0.1% to 4% by weight of a Group II metal salt of a dihydrocarbyl dithiophosphoric acid;
   (c) from about 0.3% to 10% by weight of a neutral or overbased alkali or alkaline earth metal hydrocarbyl sulfonate or mixtures thereof;
   (d) from about 0.2% to 27% by weight of a neutral or overbased alkali or alkaline earth metal alkylated phenate or mixtures thereof.

6. A method for reducing fuel consumption of an internal combustion engine comprising treating the moving surfaces thereof with a composition according to claim 4.

7. A method for reducing fuel consumption of an internal combustion engine comprising treating the moving surfaces thereof with a composition according to claim 5.

8. A normally liquid alkyl catechol as defined in claim 1 wherein the $C_{18}$ alkyl content is less than 15%.

* * * * *